(12) United States Patent
Chander et al.

(10) Patent No.: US 6,495,705 B2
(45) Date of Patent: Dec. 17, 2002

(54) EFFICIENT PROCESS FOR THE PRODUCTION OF 10-DAB III BY SELECTIVE HYDRAZINOLYSIS OF VARIOUS TAXANES

(75) Inventors: Madhavi C. Chander, Boulder, CO (US); James D. McChesney, Boulder, CO (US)

(73) Assignee: NaPro BioTherapeutics, Inc., Boulder, CO (US)

( * ) Notice: Subject to any disclaimer, the term of this patent is extended or adjusted under 35 U.S.C. 154(b) by 0 days.

(21) Appl. No.: 09/899,831

(22) Filed: Jul. 5, 2001

(65) Prior Publication Data

US 2002/0042529 A1 Apr. 11, 2002

Related U.S. Application Data

(63) Continuation-in-part of application No. 09/527,007, filed on Mar. 16, 2000, now Pat. No. 6,281,368.

(51) Int. Cl.$^7$ .............................................. C07D 305/14
(52) U.S. Cl. ........................................ 549/510; 549/511
(58) Field of Search ................................. 549/510, 511

(56) References Cited

U.S. PATENT DOCUMENTS

| | | |
|---|---|---|
| 5,202,448 A | 4/1993 | Carver et al. |
| 5,256,801 A | 10/1993 | Carver et al. |
| 5,393,895 A | 2/1995 | Gaullier et al. |
| 5,393,896 A | 2/1995 | Margraff |
| 5,453,521 A | 9/1995 | Gaullier et al. |
| 5,736,366 A | 4/1998 | Margraff |
| 5,750,736 A | 5/1998 | Sisti |
| 5,914,411 A | 6/1999 | Sisti et al. |
| 6,002,025 A | 12/1999 | Page et al. |

OTHER PUBLICATIONS

"Modified Taxols. 3. Preparation and Acylation of Baccatin, III", *Journal of Organic Chemistry*, Magri et al, 1986, 51, 3239–3242.

Structure–Activity Relationships of Taxol: Synthesis and Biological Evaluation of C2 Taxol Analogs, *Bioorg. Med. Chem. Lett.*, Chen. et al, 1994, 4, 479–482.

"Unexpectedly Facile Hydrolysis of the 2–Benzoate Group of Taxol and Syntheses of Analogs with Increased Activities", *J. Am. Chem. Soc.*, Chaudhary et al, 1994, 116, 4097–4098.

"Internal Nucleophile Assisted Selective Deesterification Studies on Baccatin III. Synthesis of 2–Debenzoyl–and 4–Decetylbaccatin III Analogues", *J. Org. Chem.*, Datta et al, 1994, 59, 4689–4690.

"Selective Deesterification Studies on Taxanes: Simple and Efficient Hydrazinolysis of C–10 and C–13 Ester Functionalities", *J. Org. Chem.*, Datta et al., 1995, 60, 761–763.

*Primary Examiner*—Ba K. Trinh
(74) *Attorney, Agent, or Firm*—Timothy J. Martin; Michael R. Henson; Rebecca A. Gegick

(57) ABSTRACT

The present invention describes a process for producing 10-deacetyl baccatin III from a solution containing a solvent reactive with hydrazine hydrate and a spectrum of taxanes. The solution is contacted with hydrazine hydrate thereby converting some taxanes therein into 10-deacetyl baccatin III. The process can target taxanes having an ester functionality on at least one of the C-10 and C-13 positions. The hydrazine hydrate cleaves the ester functionality of the taxane solute, The process may be used to produce 10-deacetyl baccatin III from a biomass extract by contacting the biomass extract with a mixture of a solvent and a hydrazine hydrate. The solvent may have a functional group that is cleaved by hydrazine. Acetate solvents are contemplated.

45 Claims, No Drawings

EFFICIENT PROCESS FOR THE PRODUCTION OF 10-DAB III BY SELECTIVE HYDRAZINOLYSIS OF VARIOUS TAXANES

CROSS-REFERENCE TO RELATED APPLICATIONS

The present application is a continuation-in-part of Application No. 09/527,007, filed Mar. 16, 2000, now U.S. Pat. No. 6,281,368.

FIELD OF THE INVENTION

The present invention generally relates to the purification of a biomass extract to form useful materials. More particularly, the present invention is directed to the conversion of unwanted taxanes in a biomass extract to taxanes that can be used in the synthesis of paclitaxel. Specifically, the present invention relates to the conversion of unwanted taxanes into 10-deacetyl baccatin III, a useful precursor in the formation of paclitaxel.

BACKGROUND OF THE INVENTION

Various taxane compounds are known to exhibit anti-tumor activity. As a result of this activity, taxanes have received increasing attention in the scientific and medical community. Primary among these is a compound known as "paclitaxel" which is also referred to in the literature as "taxol". Paclitaxel has been approved for the chemotherapeutic treatment of several different varieties of tumors, including refractory ovarian and metastatic breast cancers. Clinical trials, including those for the treatment of lung, head, neck and other cancers, indicate that paclitaxel promises a broad range of potent anti-leukemic and tumor-inhibiting activity. Further development of this pharmaceutical lead and identification of its superior analogs is crucial to continued advancement of cancer chemotherapy.

Paclitaxel has the formula and numbering as follows:

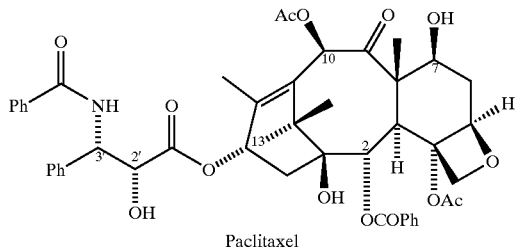

Paclitaxel

Paclitaxel is a naturally occurring taxane diterpenoid which is found in several species of the yew (genus Taxus, family Taxaceae). Unfortunately, the concentration of this compound is very low. The species of evergreen yew are also slow growing. Even though the bark of the yew trees typically exhibit the highest concentration of paclitaxel, the production of one kilogram of paclitaxel requires approximately 16,000 pounds of bark. Thus, the long term prospects for the availability of paclitaxel through isolation are discouraging.

Accordingly, numerous efforts have been directed to the partial synthesis of paclitaxel from closely related precursor compounds. While the presence of paclitaxel in the yew tree is in extremely low concentrations, there are a variety of other taxane compounds, such as Baccatin III, cephalommanine, 10-deacetyl baccatin III, etc., which are also able to be extracted from the yew. Some of these other taxane compounds are more readily extracted in higher yields.

In order to successfully synthesize paclitaxel, convenient access to a chiral, non-racemic side chain and an abundant natural source of a usable baccatin III backbone as well as an effective means of joining the two are necessary. However, the esterification of the side chain to the protected baccatin III backbone is difficult because of the sterically hindered C-13 hydroxyl in the baccatin III backbone which is located within the concave region of the hemispherical protected baccatin III skeleton. Techniques have been developed for the partial synthesis of paclitaxel from the naturally occurring diterpenoid substances baccatin III and closely related 10-deacetyl baccatin III ("10-DAB III"), which accordingly have become important precursors for use in synthetic routes to paclitaxel. Baccatin III and 10-DAB III have the formulas as follows:

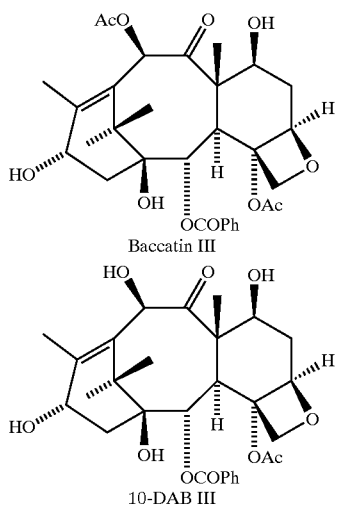

Baccatin III

10-DAB III

10-DAB III is more abundant in nature than is baccatin III. Indeed, a relatively high concentration of 10-DAB III can be extracted from the leaves of the yew as a renewable resource. Co-occurring with paclitaxel, baccatin III and 10-DAB III in biomass are several closely related taxanes containing the same diterpenoid structure element of baccatin III or 10-DAB III. They are removed as side stream products during usual purification procedures for paclitaxel or 10-DAB III. These side stream products include cephalomannine, nitine, taxol C, 7-xylosyl taxols, 10-deacetyl taxol, and several other taxanes and non-taxanes. As shown in Table 1, many of these taxanes have the same general backbone structure as follows:

TABLE 1

| Product | $R_1$ | $R_2$ |
|---|---|---|
| CEPHALOMANNINE | tigloyl | Ac |
| NITINE | phenyl acetyl | Ac |
| TAXOL C | hexanoyl | Ac |
| 10-DEACETYL TAXOL | benzoyl | H |

Although these side stream products have general structures similar to the structures of paclitaxel, baccatin III and 10-DAB III, they are currently left over as unusable waste products of the purification processes for paclitaxel or 10-DAB III. Accordingly, it would be desirable to convert such leftover side stream products into usable materials for paclitaxel synthesis, thereby to increase the availability of this important anti-cancer agent.

Only a few methods have been reported for the selective hydrolysis of the various ester groups present in paclitaxel. Magri et al have reported on the selective reductive cleavage of the C-13 side chain of paclitaxel, using tetrabutyl ammonium borohydride (Journal of Organic Chemistry, 1986, 51, 3239–3242). U.S. Pat. Nos. 5,202,448 and 5,256,801 to Carver et al. teach the conversion of partially purified taxane mixtures into baccatin III and 10-DAB III using a borohydride reducing salt in the presence of a Lewis acid.

The selective hydrolysis of the benzoate group at C-2 has been achieved by three research groups. In one method by Chen et al, a 7,13-diprotected baccatin III with Red-Al afforded the corresponding 2-debenzoylated derivative in 78% yield (Bioorg. Med. Chem. Lett. 1994, 4, 479–482). In another method, reported by Chaudhary et al, hydrolysis of 2',7-diprotected paclitaxel with NaOH under phase transfer conditions formed the corresponding 2-debenzoylpaclitaxel derivative in moderate yield (J. Am. Chem. Soc., 1994,116, 4097). In a third method, reported by Datta et al, selective deesterification of baccatin III derivatives at C-2 and C-4 was achieved in 69% and 58% yields respectively with potassium tert-butoxide as base (J. Org. Chem., 1994, 59, 4689–4690).

Appurba Datta, Michael Hepperle, and Gunda I. Georg have also reported, in J. Org. Chem, 1995, 60, 761–63, selective deesterification processes to remove the C-10 and C-13 ester functionalities of pure cephalomannine and paclitaxel by hydrazinolysis. That work was encouraged by a recognition that both ammonia and hydrazine are used for the removal of ester groups under mild conditions wherein acetates are preferentially cleaved over benzoate groups. Datta, Hepperle and Georg reported that a solution of paclitaxel in 95% ethanol that was treated with hydrazine monohydrate at room temperature for two hours yielded 10-DAB III as the only product obtained. The 10-DAB III product was formed by cleavage of the ester linkages of paclitaxel at C-10 and C-13. Datta, Hepperle and Georg extended this reaction to a National Cancer Institute mixture of mainly paclitaxel and cephalomannine with some other minor impurities, which cleanly yielded 10-DAB III when reacted with hydrazine monohydrate. The reactions reported by Datta, Hepperle and Georg utilizing a hydrazine monohydrate solution in 95% ethanol were at a pH of about 10, such that the hydrazine monohydrate, a strong base, is reactive to cleave ester groups similarly to other basic nucleophiles.

However, there remains a need to provide simple and efficient methods to convert sidestream products from extraction processes, which generally result in highly acidic biomass extracts, into usable products such as 10-DAB III. In particular, there remains a need for a process to convert a complex mixture of taxanes, such as one containing cephalomannine, 10-deacetyl taxol, baccatin III and several other taxanes in a relatively unpurified or partially purified form, to 10-DAB III which can be purified and utilized for semi-synthesis purposes to synthesize paclitaxel and its analogs. The present invention is directed to meeting these needs.

SUMMARY OF THE INVENTION

It is an object of the present invention to provide a new and useful process for the conversion of sidestream products from taxane extraction processes into usable products for paclitaxel synthesis.

It is another object to provide a simple and efficient method to convert a complex mixture of taxanes into paclitaxel precursor products.

It is yet another object to produce useful synthetic precursors from a biomass extract using desirable solvents.

A still further object is to produce relatively pure 10-DAB III from a mixture of taxanes such as cephalomannine, 10-deacetyltaxol, baccatin III and several other taxanes.

Yet another object is to produce 10-DAB III useful in paclitaxel synthesis from a biomass extract containing taxanes that have ester functionalities at the C-10 and/or C-13 positions.

According to the present invention, then, a process is provided for producing 10-deacetyl baccatin III, comprising contacting a first solution including a solvent and a spectrum of taxanes with a hydrazine hydrate, thereby to convert into 10-deacetyl baccatin III some taxanes in said solution that are not 10-deacetyl baccatin III, wherein the solvent is one that is reactive with hydrazine hydrate. More particularly, the solvent may include a functional group that is cleaved by hydrazine, such as an ester functionality. Specifically, the solvent may be an acetate solvent such as isobutyl acetate, isopropyl acetate or ethyl acetate. The first solution may be concentrated or diluted to a ratio of 1.0 mL of solvent per 0.10 g of total dissolved solids in the first solution prior to contacting the first solution with the hydrazine hydrate. The hydrazine hydrate is preferably hydrazine monohydrate, in a range of from 0.6 mL to 4.0 mL of hydrazine monohydrate per 1.0 g of total dissolved solids in the first solution, and preferably approximately 2.0 mL of hydrazine monohydrate per 1.0 g of total dissolved solids.

A biphasic solution may be formed by the step of contacting the first solution with a hydrazine hydrate, and 10-deacetyl baccatin III may be recovered from the biphasic solution by separating an organic layer and an aqueous layer thereof. Preferably, the biphasic solution is stirred for 45 minutes to one hour at ambient temperature prior to separating the organic and aqueous layers. The organic layer may be contacted with activated carbon or passed through an adsorption column, and 10-deacetyl baccatin III may be crystallized from the organic layer using acetonitrile as an anti-solvent, and re-crystallized from methanol using acetonitrile as an anti-solvent.

The present invention also provides a process for producing 10-deacetyl baccatin III from a biomass extract that contains as a constituent thereof at least one taxane that has an ester functionality on at least one of the C-10 and C-13 positions. The process comprises contacting the biomass extract with a solvent, thereby to form a first solution that contains at least one taxane solute that has an ester functionality on at least one of the C-10 and C-13 positions, where the solvent is one that is reactive with hydrazine hydrate; and contacting the first solution with a hydrazine hydrate, thereby to cleave the ester functionality of the taxane solute. The biomass extract may be derived from a plant of the genus Taxus, and is preferably adsorbed onto a suitable substrate, such as silica gel, silica, sand or diatomaceous earth, prior to contacting the biomass extract with the solvent.

Additionally, the present invention provides a process for producing 10-deacetyl baccatin III from a biomass extract derived from a plant of the genus Taxus, comprising contacting the biomass extract with a mixture of a solvent and a hydrazine hydrate, thereby to convert into 10-deacetyl baccatin III some taxanes in the biomass extract that are not 10-deacetyl baccatin III, wherein the solvent is one that is reactive with hydrazine hydrate.

These and other objects of the present invention will become more readily appreciated and understood from a consideration of the following detailed description of the exemplary embodiments of the present invention

DETAILED DESCRIPTION OF THE EXEMPLARY EMBODIMENTS

The present invention provides an alternative to the hydrazinolysis process disclosed in Application No. 09/527,007, filed Mar. 16, 2000, now U.S. Pat. No. 6,281,368. As discussed therein, a complex mixture of taxanes containing cephalomannine, 10-deacetyl taxol, baccatin III and several other taxanes in an unpurified form derived from biomass may be converted with hydrazine hydrate to 10-DAB III, which is purified and utilized for the semi-synthesis of paclitaxel and its analogs. Notably, that application describes the use of various solvents, and preferably alcohol solvents such as ethanol or methanol, in the hydrazinolysis process.

The present invention, however, relates to the use of certain solvents, such as acetate solvents, that are reactive toward hydrazine, and thus would be expected to quench any hydrazine activity toward the ester functionality of taxane solutes in the solution. In particular, it has been discovered that solvents having an ester functionality that is cleaved by hydrazine, such as isopropyl acetate (IPAc), isobutyl acetate (IBAc), ethyl acetate (EtOAc) and the like, provide beneficial results when used in place of alcohol solvents in the hydrazinolysis process described in application Ser. No. 09/527,007. Specifically, the use of such acetate solvents provides less unwanted total dissolved solids, an easier work-up and decreased reaction times over the use of alcohol solvents in the hydrazinolysis reaction.

For example, biomass extract extracted with IPAc, IBAc or EtOAc, and preferably IBAc or IPAc, has all the accountable taxanes compared to biomass extract extracted with methanol (MeOH), but contains less total dissolved solids (TDS) and is much lighter in color. The presence of lower amounts of TDS in the reaction mixture permits the reaction to proceed in a much cleaner fashion. In particular, the reaction requires smaller amounts of hydrazine hydrate reagent, has shorter reaction times, and provides a higher purity product, thus requiring fewer processing steps before further utilization of the worked-up product.

Additionally, after the addition of hydrazine to a solution of IPAc or IBAc containing the extracted taxanes, the reaction mixture becomes biphasic with a very dark brown colored bottom aqueous layer and a pale yellow to light brown colored upper organic layer, which does not require any additional effort in partitioning the two layers. By contrast, additional solvent was added to the reaction with MeOH solution to separate the organic layer in a particular order and composition. Moreover, the reaction with MeOH utilized additional extraction of the aqueous layers to extract all the 10-DAB III derived from the hydrazinolysis.

Further, the reaction time is substantially shorter when using acetate solvents versus using alcohol solvents. For example, reactions using IPAc or IBAc solutions were shown to go to completion in approximately 45 minutes, versus up to 3 hours for solution using alcohol solvents.

The beneficial results provided by the use of solvents that react with hydrazine, and acetate solvents like IPAc, IBAc or EtOAc in particular, are unexpected, and this reaction provides a surprising result. Because the solvent itself is reactive toward hydrazine, the ordinarily skilled person would expect the solvent to greatly reduce or quench any hydrazine reactivity toward the taxane ester functionalities. Indeed, as shown in Table 2 below, experiments reacting hydrazine alone with IPAc, IBAc and EtOAc produced the respective alcohols thereof, thus demonstrating that hydrazine does in fact react with the solvent thereby to cleave the respective ester functionality thereof. In particular, 1.0 mL of hydrazine monohydrate was respectively added to each of a volume of 4.5 mL of IBAc, IPAc and EtOAc. The resulting biphasic mixtures were agitated for 1.0 h and GC analysis of the same confirmed the generation of the respective alcohols.

TABLE 2

| volume of hydrazine monohydrate | volume and type of solvent | respective alcohol of solvent observed? |
| --- | --- | --- |
| 1.0 mL | 4.5 mL IBAc | YES |
| 1.0 mL | 4.5 mL IPAc | YES |
| 1.0 mL | 4.5 mL EtOAc | YES |

These experiments confirmed that hydrazine monohydrate reacts with the acetate solvents by themselves, such that the hydrazine monohydrate would be expected to be consumed upon addition to a solution having an acetate solvent.

The process of the present invention provides a surprising result in that it would be expected (and experimental results demonstrate) that hydrazine hydrate would react with and cleave the ester functionality of the solvent. This would be expected to completely or substantially reduce the reactivity of hydrazine toward the taxanes in the solution. The results of this reaction are even more surprising in view of the fact that the reaction appears to proceed to completion much faster than with alcoholic solvents. Accordingly, this process provides an unexpected yet efficient route to utilize the byproduct side stream taxanes without tedious purification procedures and to convert these taxanes to an essential taxane, 10-DAB III, the building block for semi-synthesis of paclitaxel, docetaxel, and analogs thereof.

I Preparation of Biomass Extract

The present invention utilizes biomass extract, which may be partially or minimally purified, and which is derived from a plant of the genus Taxus. Specifically, the biomass extract may be derived from yew varieties such as *Taxus baccata, Taxus brevifolia, Taxus canadensis, Taxus cuspidata, Taxus floridana, Taxus media* and *Taxus wallichiana*. Such biomass extracts contain various taxanes, such as cephalomannine, 10-deacetyl taxol, baccatin III and other taxanes, as well as a range of other materials, such as plant materials including phenolic materials and carboxylic acids. Generally, the biomass extract is composed of only a few weight percent, such as approximately five percent (5%), taxanes. The remainder is composed of other biomass derived substances such as acidic plant materials. The biomass extracts used in the present invention are generally aqueous alcohol extracts of Taxus biomass that have been treated to remove therefrom some plant materials such as chlorophyl and plant pigments, as well as the majority of paclitaxel.

The production of such biomass extracts is commonly known in the art. Exemplary methods for producing biomass extracts for use in the present invention are described in part, for example, in U.S. Pat. No. 5,393,895 to Gaullier et al., and U.S. Pat. Nos. 5,393,896 and 5,736,366 to Margraff. The teachings of those references are incorporated herein by reference. In particular, as discussed in the Gaullier et al.

patent, one process for the production of biomass extracts for use in the present invention begins with stirring an optionally heated mixture of ground yew vegetable matter and an aliphatic alcohol, such as methanol, to obtain an alcoholic extract. The ground yew vegetable matter may be derived from any appropriate part of the yew, and may be obtained by grinding and optionally drying operations to obtain fragments of yew. In obtaining such fragments, freezing and thawing operations directed to the fresh parts of the plant may be optionally utilized as well.

The alcoholic extract, which may first be concentrated, is next diluted with water to form a hydroalcoholic solution. Products that are insoluble in the hydroalcoholic solution are then removed, such as by filtration, centrifugation or settling. Virtually all of the alcohol is then removed from the hydroalcoholic solution, such as by distillation at reduced pressure. The remaining aqueous solution is then extracted with an organic solvent, such as an ether or aliphatic ester, the organic extract is optionally washed with water and/or an aqueous solution of a weak base, and dried. The organic solvent is next removed, such as by distillation at reduced pressure, to produce a residue.

The remaining residue constitutes a biomass extract for use in the hydrazinolysis reaction described below. It should be appreciated that this biomass extract contains 10-DAB III as well as taxane constituents having an ester functionality on at least one of the C-10 and C-13 positions, such as cephalomannine, 10-deacetyl taxol, baccatin III and other taxanes. It has been found that 10-DAB III is stable under the reaction conditions for the hydrazinolysis reaction described below, such that the present invention makes it possible to obtain good yields of 10-DAB III from yew vegetable matter without requiring an extra step of first isolating and removing any 10-DAB III extracted by the above process.

Additional processes for the production of biomass extracts for use in the present invention are discussed, for example, in the Margraff patents. Although generally similar to the process taught by Gaullier et al., Margraff teaches that ground yew vegetable matter is first stirred with water, such as at a temperature of 20° to 65° C. for a time interval of 30 minutes to 2 hours. The aqueous solution obtained is then separated from the vegetable matter remaining in suspension, such as by filtration, centrifugation or settling, and optionally may be cooled.

Taxanes may next be extracted from the aqueous solution by adding an organic solvent thereto, such as an ether or aliphatic ester. The organic extract is separated from the aqueous phase, is optionally washed with water and/or an aqueous solution of a weak base, and dried, after which the organic solvent is removed, such as by distillation at reduced pressure, to produce a residue.

As an alternative to extraction, the aqueous solution may be adsorbed on a suitable substrate, such as an adsorbing resin, which is then washed with a suitable solvent, such as methanol. The resulting solution is then separated from the substrate, such as by filtration, and concentrated to dryness, such as by distillation at reduced pressure, to produce a residue.

As with the residue produced according to the teachings of the Gaullier et al. reference, such a residue produced according to either of the processes taught by the Margraff references constitutes a biomass extract for use in the hydrazinolysis reaction described below. Again, it should be appreciated that this biomass extract contains 10-DAB III as well as taxane constituents having an ester functionality on at least one of the C-10 and C-13 positions.

Alternatively, as discussed in the Gaullier et al. and Margraff references, 10-DAB III may first be removed from the residue prior to the hydrazinolysis reaction described below. This is accomplished by selective crystallization of 10-DAB III from a solution of the residue in one or more organic solvents, which may include acetonitrile. The 10-DAB III precipitate is separated from the residue solution, such as by filtration, centrifugation or settling. The solution remaining after the removal of the 10-DAB III forms an alternative biomass extract for use in the hydrazinolysis reaction of the present invention. Additionally, the solution remaining after the removal of 10-DAB III may be concentrated, such as by distillation at reduced pressure, to form a further alternative version of the biomass extract.

It should be appreciated that after the removal of 10-DAB III, the resulting biomass extract still contains taxane constituents having an ester functionality on at least one of the C-10 and C-13 positions, such as cephalomannine, 10-deacetyl taxol, baccatin III and other taxanes. Furthermore, it should be noted that, while a biomass extract resulting from the above processes may have been partially purified by partitioning between organic and aqueous layers, it has not been subjected to purification by HPLC. In particular, the process of the present invention is desirable in that it minimizes the need for such additional purification steps, thus affording an attractive and efficient route to recovering and using otherwise unusable taxanes.

II. Production and Purification of 10-DAB III from Biomass Extract

The present invention provides an efficient method for the selective transformation of a complex mixture of taxanes by deesterification of ester functionalities thereof, and in particular the C-10 and C-13 ester functionalities thereof. The process utilizes biomass extract produced as sidestream products from taxane extraction processes, such as described above.

A. Hydrazinolysis Reaction

An exemplary reaction according to the present invention is as follows:

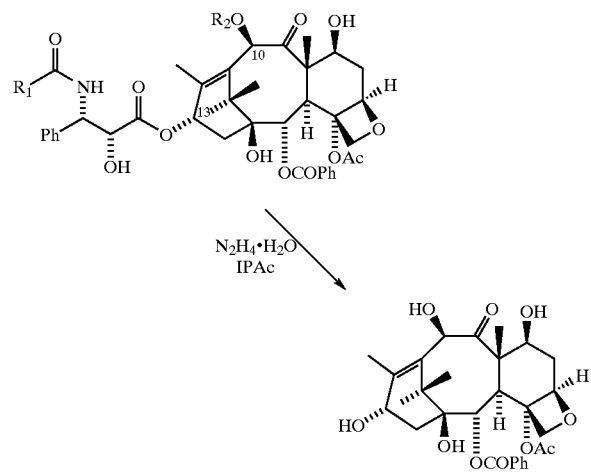

wherein $R_1$ can be an alkyl group, an olefinic group, an aromatic group, hydrogen or a group containing oxygen, nitrogen or sulfur; and $R_2$ can be hydrogen or $R_3C{=}O$ wherein $R_3$ is an alkyl group. $R_1C{=}O$ can specifically be benzoyl, tigloyl, phenyl acetyl, or hexanoyl, and $R_3C{=}O$ can specifically be acetyl.

As demonstrated in the above reaction, the ester functionalities at the C-10 and C-13 positions are cleaved by hydrazinolysis. It should be understood that where the C-10 position includes a hydroxyl group bonded thereto (i.e., $R_2$ is H) such that no C-10 ester functionality is present, only the C-13 side chain is affected. Furthermore, it should be appreciated that the above-illustrated chemical structures are not exhaustive of all possible moieties for taxanes found in biomass extract that have the general taxane backbone found in 10-DAB III, and which may be reacted according to the present invention.

It should further be appreciated that, while IPAc is shown as the solvent in the exemplary process, other solvents that are reactive with hydrazine are contemplated for use in the process of the present invention. In particular, solvents having a functionality that is cleaved by hydrazine, such as an ester functionality, are contemplated, and in particular solvents such as IPAc, IBAc, EtOAc and the like. Additionally, the present invention contemplates the use of other solvents, including acetonitrile, ether solvents such as THF, and the like, which may be used in the hydrazinolysis reaction, to the extent understood by the ordinarily skilled artisan.

In the preferred embodiment, a solution is formed containing a spectrum of taxanes having ester functionalities at the C-10 position, C-13 position or both. This solution is formed by contacting a biomass extract prepared as described above with IPAc, IBAc, EtOAc or another solvent that is reactive toward hydrazine. In particular, it is preferred that the solvent extraction is performed on biomass extract that is adsorbed onto silica gel and packed in a column. It should be appreciated that silica gel may be substituted with other suitable substrates, such as silica, sand, diatomaceous earth or other high surface area non-reactive substrates. Alternatively, the solvent may be directly mixed with the biomass extract to form the solution. In any event, the weight percent of taxanes in the solution is generally less than five percent (5%). The solution is preferably concentrated to a ratio of 1.0 mL / 0.10 g of total dissolved solids using a rotary evaporator at $\leq 55°$ C. To this solution is added a hydrazine hydrate, preferably hydrazine monohydrate (64% hydrazine by weight), at a preferred ratio of 2.0 mL/1 g of total dissolved solids present in the solution. The resulting reaction mixture is stirred at ambient temperature for about 45 minutes. Several samples for HPLC analysis were obtained for reactions times of 15 minutes, 30 minutes, 45 minutes and 60 minutes, respectively. The reactions for various taxane-containing solutions were typically done by 30 minutes and were worked up by 45 minutes. Reactions were monitored by sampling periodically over 24 hours, and the optimal reaction time was determined to be 45 minutes. The preferred balance of reaction rate and 10-DAB III yield was found using a 2.0 mL hydrazine hydrate /1 g total dissolved solids ratio at a solution concentration of 1 mL IPAc or IBAc/0.10 g total dissolved solids, which allowed a reaction duration of 45 minutes.

As shown in Tables 3–5 below, several hydrazinolysis reactions were performed using different acetate solvents. In particular, Tables 3, 4 and 5 show reactions performed with IBAc, IPAc and EtOAc solvents, respectively. The data in the following tables show HPLC area% of 10-DAB III and 10-deacetyltaxol (10-DAT) measured over time. The selective deesterification of various taxanes in the solution to form 10-DAB III is confirmed by the increase in concentrations of 10-DAB III and the disappearance of 10-DAT. While 10-DAT was used here as a measure of the completeness of the reaction, it should be appreciated that other taxanes in the solution are also converted to 10-DAB III by the hydrazinolysis reaction. It should also be noted that prolonged reaction times, particularly beyond the 3.0 h time point, showed the production of 10-DAB V (the epimerized product of 10-DAB III at the 7-position). Also, as shown in Table 5, the reaction in EtOAc is slower than those in the other acetate solvents.

TABLE 3

(IBAc solvent)

|  | 0.0 h | 0.5 h | 1.5 h | 3.0 h | 6.0 h | 23 h |
|---|---|---|---|---|---|---|
| 10-DAB III | 34.7 | 76.7 | 83.2 | 80.0 | 80.9 | 80.7 |
| 10-DAT | 28.5 | 3.1 | 0.0 | 0.0 | 0.0 | 0.0 |

TABLE 4

(IPAc solvent)

|  | 0.0 h | 0.5 h | 1.5 h | 3.0 h | 6.0 h | 23 h |
|---|---|---|---|---|---|---|
| 10-DAB III | 34.7 | 89.5 | 90.7 | 79.2 | 74.0 | 72.4 |
| 10-DAT | 28.5 | 0.0 | 0.0 | 0.0 | 0.0 | 0.0 |

TABLE 5

(EtOAc solvent)

|  | 0.0 h | 0.5 h | 1.5 h | 3.0 h | 6.0 h | 23 h |
|---|---|---|---|---|---|---|
| 10-DAB III | 34.7 | 58.3 | 66.8 | 67.2 | 74.5 | 79.0 |
| 10-DAT | 28.5 | 17.7 | 13.6 | 11.9 | 9.8 | 0.0 |

Accordingly, as apparent from Tables 3–5 above, the use of various solvents that are reactive with hydrazine, and acetate solvents in particular, in the hydrazinolysis reaction provides a simple and efficient, yet surprising, method for the conversion of various taxanes in the solution to 10-DAB III.

Several ratios of hydrazine hydrate to total dissolved solids have been tested with methanol solvent, although it should be appreciated that similar ratios of hydrazine hydrate to total dissolved solids are believed to work with other solvents, such as acetate solvents as described herein. In particular, 3, 4 and 5 hour reactions were performed at varying ratios of between 0.6 mL and 4.0 mL hydrazine hydrate to total dissolved solids at solvent to total dissolved solids solution concentrations of 1 mL methanol to between 0.1 g and 0.15 g total dissolved solids. These reactions were performed using partially purified methanolic extracts of Taxus biomass. To monitor the reaction rate, the concentration of 10-deacetyl taxol expressed as a relative area percent of 10-DAB III was measured.

Specifically, the reaction rates and 10-DAB III yield were measured for 4 and 5 hour reactions at a 0.6 mL hydrazine monohydrate/g total dissolved solids ratio, and for 3 hour reactions at ratios of 0.6 mL, 1.0 mL, 1.2 mL, 1.9 mL, 2.0 mL, 2.4 mL, 3.0 mL and 4.0 mL hydrazine hydrate/g total dissolved solids. It was found that too low of a hydrazine hydrate to total dissolved solids ratio resulted in a longer time period for complete reaction, whereas too high of a hydrazine hydrate to total dissolved solids ratio resulted in lower 10-DAB III yields. It should be appreciated that in commercial processes, shorter reaction times are desirable to the extent that acceptable yields are maintained.

It should further be appreciated that the present invention contemplates a hydrazinolysis reaction wherein the biomass extract is directly contacted with a mixture of a solvent of the type described above, and a hydrazine hydrate, preferably hydrazine monohydrate. It is believed that in such a case the hydrazine hydrate will cleave the C-10 and C-13 ester functionalities of taxanes present in the biomass extract, thereby to convert such taxanes into 10-DAB III, despite the presence of a similar functionality in the solvent that would be expected to quench the hydrazine reactivity toward the taxanes. The biomass extract may alternatively be adsorbed onto a suitable substrate prior to being contacted with the mixture.

B. Recovery and Purification of 10-DAB III

The reaction solution after the addition of hydrazine becomes biphasic with a very dark brown colored bottom aqueous layer and a pale yellow to light brown colored upper organic layer. The biphasic reaction mixture is stirred vigorously for 45 minutes to 1 hour before allowing the phases to separate. It should be recognized that the taxanes are partitioned into the top organic layer and the hydrazine and any salts that are formed are partitioned into the bottom aqueous layer, and the organic layer is separated therefrom. It is believed that no significant percentage of 10-DAB III remains in the aqueous layer.

Alternatively, the solution may be quenched with a suitable quenching agent, such as with a dilute acid solution or aqueous ammonium chloride solution, although this quenching step can increase the time requirement for the total process by 3 to 5 hours. When the hydrazinolysis reaction is not quenched, it is preferred that the reaction is partitioned quickly after the desired reaction time to separate the hydrazine from the taxanes. It is believed that reactions that are not partitioned quickly could result in lower 10-DAB III yields, as a result of decomposition of some 10-DAB III in the solution, because the reaction of hydrazine with the taxanes will continue until the hydrazine is separated therefrom.

The separated organic layer is preferably washed with water (2 times with 20% v/v of the organic layer) and brine (1 time with 20% v/v of the organic layer). To the organic phase at this stage was added powdered, activated carbon (preferably 0.5g of carbon/1.0 g of total dissolved solids of the organic phase) and is stirred at ambient temperature for 1 h and filtered.

Alternatively, the organic layer recovered from the above partitioning step may be passed through a carbon/alumina/silica adsorption column to reduce total dissolved solids and color. The use of an adsorption column after the hydrazinolysis and prior to the crystallization steps outlined below assists in maximizing the 10-DAB III yield through the prevention of precipitate formation during concentration for crystallization. The column preferably contains layers of granular activated carbon, alumina N1 and silica gel in this order from top to bottom. The preferred ratios are 0.5 g of carbon, 1.0 g of alumina Ni and 1.0 g of silica gel per 1.0 g of total dissolved solids in the organic solution. After passing the organic layer through the column in a downward flow, the column is preferably eluted with approximately three (3) column volumes of isobutyl acetate and the rinse combined with the solution.

The resulting solution is preferably concentrated on a rotary evaporator at $\leq 55°$ C. to a total dissolved solids residue of approximately 0.3 g/mL and acetonitrile (MeCN) is preferably added (approximately 10% of the total volume) as an anti-solvent, such that a crystallization of the 10-DAB III in acetate solvent with acetonitrile may be performed. The low solubility of 10-DAB III in acetonitrile, contrasted with good solubility of most other compounds in acetonitrile, makes it an ideal anti-solvent for 10-DAB III crystallizations. The resulting mixture is stirred at ambient temperature for at least five (5) hours during which time a solid precipitate forms. The solid obtained is filtered and the filter cake washed with 9:1 acetate solvent and acetonitrile solution at a ratio of 1.0 mL/1.0 g of total dissolved solids.

The washed solid is preferably dissolved in methanol at a ratio of 30 mL/1.0 g of total dissolved solids in the isobutyl acetate concentrate, and this solution is filtered through a 1 $\mu$m filter. The filtered methanol solution is preferably concentrated on a rotary evaporator at $\leq 55°$ C. to a residue of approximately 0.133 g/mL and a crystallization of the 10-DAB III in methanol with acetonitrile as an anti-solvent is performed by adding acetonitrile (40% of the total volume) at ambient temperature with continuous stirring for five (5) hours. The solid formed is filtered and the filter cake washed with methanol and acetonitrile (7:3, v:v) at a ratio of 4 mL/1.0 g of total dissolved solids in the methanol solution. The solid is dried in a vacuum oven at $\leq 80°$ C. for at least sixteen (16) hours to reduce the concentration of residual methanol to $\leq 0.5\%$ by weight. Such a reduction of methanol is desirable in that methanol has been found to interfere with the acetylation of 10-DAB III in the paclitaxel synthetic process.

The 10-DAB III at this stage is >95% by HPLC area and is suitable as a starting material for the semi-synthesis of paclitaxel, docetaxel, and analogs thereof. It should be noted that 10-DAB III mother liquors and rinses resulting from the above purification steps can be recycled using multiple methanol/acetonitrile crystallizations, to increase the overall 10-DAB III yield.

Accordingly, the present invention has been described with some degree of particularity directed to the exemplary embodiment of the present invention. It should be appreciated, though, that the present invention is defined by the following claims construed in light of the prior art so that modifications or changes may be made to the exemplary embodiment of the present invention without departing from the inventive concepts contained herein.

We claim:

1. A process for producing 10-deacetyl baccatin III, comprising contacting a first solution including a solvent and a spectrum of taxanes with a hydrazine hydrate, thereby to convert into 10-deacetyl baccatin III some taxanes in said solution that are not 10-deacetyl baccatin III, wherein said solvent is one that is reactive with hydrazine hydrate.

2. A process according to claim 1 wherein said solvent includes a functional group that is cleaved by hydrazine.

3. A process according to claim 1 wherein said solvent includes an ester functionality.

4. A process according to claim 1 wherein said solvent is an acetate solvent.

5. A process according to claim 1 wherein said solvent is selected from isobutyl acetate, isopropyl acetate and ethyl acetate.

6. A process according to claim 1 wherein said solvent is selected from isobutyl acetate and isopropyl acetate.

7. A process according to claim 6 wherein 10-deacetyl taxol in said first solution is converted to 10-deacetylbaccatin III within 1.5 hours after contacting said first solution with said hydrazine hydrate.

8. A process according to claim 7 wherein 10-deacetyl taxol in said first solution is converted to 10-deacetylbaccatin III within 30 minutes after contacting said first solution with said hydrazine hydrate.

9. A process according to claim 1 wherein said first solution is at a ratio of 1.0 mL of said solvent per 0.10 g of total dissolved solids in said first solution prior to contacting said first solution with said hydrazine hydrate.

10. A process according to claim 1 wherein said hydrazine hydrate is hydrazine monohydrate.

11. A process according to claim 10 wherein said first solution is contacted with from 0.6 mL to 4.0 mL of hydrazine monohydrate per 1.0 g of total dissolved solids in said first solution.

12. A process according to claim 11 wherein said first solution is contacted with approximately 2.0 mL of hydrazine monohydrate per 1.0 g of total dissolved solids in said first solution.

13. A process according to claim 1 including the step of adding a suitable quenching agent after the step of contacting said first solution with a hydrazine hydrate.

14. A process according to claim 13 wherein said quenching agent is selected from the group consisting of a dilute acid solution and aqueous ammonium chloride solution.

15. A process according to claim 1 wherein a biphasic solution is formed by the step of contacting said first solution with a hydrazine hydrate, and wherein 10-deacetyl baccatin III is recovered from said biphasic solution by separating an organic layer and an aqueous layer thereof.

16. A process according to claim 15 wherein said biphasic solution is stirred for 45 minutes to one hour prior to separating said organic and aqueous layers thereof.

17. A process according to claim 16 wherein said biphasic solution is stirred at ambient temperature.

18. A process according to claim 15 wherein said organic layer of said biphasic solution includes a solvent selected from isobutyl acetate, isopropyl acetate and ethyl acetate.

19. A process according to claim 15 wherein said organic layer is contacted with activated carbon.

20. A process according to claim 15 wherein said organic layer is passed through an adsorption column.

21. A process according to claim 15 wherein 10-deacetyl baccatin III is crystallized from said organic layer using acetonitrile as an anti-solvent.

22. A process according to claim 21 wherein 10-deacetyl baccatin III is recrystallized from methanol using acetonitrile as an anti-solvent.

23. A process for producing 10-deacetyl baccatin III from a biomass extract that contains as a constituent thereof at least one taxane that has an ester functionality on at least one of the C-10 and C-13 positions, comprising:
  (a) contacting the biomass extract with a solvent, thereby to form a first solution that contains at least one taxane solute that has an ester functionality on at least one of the C-10 and C-13 positions, wherein said solvent is one that is reactive with hydrazine hydrate; and
  (b) contacting said first solution with a hydrazine hydrate, thereby to cleave the ester functionality of said taxane solute.

24. A process according to claim 23 wherein said solvent includes a functional group that is cleaved by hydrazine.

25. A process according to claim 23 wherein said solvent includes an ester functionality.

26. A process according to claim 23 wherein said solvent is an acetate solvent.

27. A process according to claim 23 wherein said solvent is selected from isobutyl acetate, isopropyl acetate and ethyl acetate.

28. A process according to claim 23 wherein said solvent is selected from isobutyl acetate and isopropyl acetate.

29. A process according to claim 23 wherein said biomass extract is derived from a plant of the genus Taxus.

30. A process according to claim 23 wherein said biomass extract is adsorbed onto a suitable substrate prior to contacting said biomass extract with said solvent.

31. A process according to claim 30 wherein said substrate is selected from silica gel, silica, sand, and diatomaceous earth.

32. A process according to claim 30 wherein said substrate is silica gel.

33. A process according to claim 23 wherein said first solution is at a ratio of 1.0 mL of said solvent per 0.1 g of total dissolved solids in said first solution prior to contacting said first solution with said hydrazine hydrate.

34. A process according to claim 23 wherein said hydrazine hydrate is hydrazine monohydrate.

35. A process according to claim 34 wherein said first solution is contacted with from 0.6 mL to 4.0 mL of hydrazine monohydrate per 1.0 g of total dissolved solids in said first solution.

36. A process according to claim 35 wherein said first solution is contacted with approximately 2.0 mL of hydrazine monohydrate per 1.0 g of total dissolved solids in said first solution.

37. A process according to claim 23 wherein a biphasic solution is formed by the step of contacting said first solution with a hydrazine hydrate, and wherein 10-deacetyl baccatin III is recovered from said biphasic solution by separating an organic layer and an aqueous layer thereof.

38. A process according to claim 37 wherein said biphasic solution is stirred for 45 minutes to one hour prior to separating said organic and aqueous layers thereof.

39. A process for producing 10-deacetyl baccatin III from a biomass extract derived from a plant of the genus Taxus, comprising contacting the biomass extract with a mixture of a solvent and a hydrazine hydrate, thereby to convert into 10-deacetyl baccatin III some taxanes in the biomass extract that are not 10-deacetyl baccatin III, wherein said solvent is one that is reactive with hydrazine hydrate.

40. A process according to claim 39 wherein said solvent includes a functional group that is cleaved by hydrazine.

41. A process according to claim 39 wherein said solvent includes an ester functionality.

42. A process according to claim 39 wherein said solvent is an acetate solvent.

43. A process according to claim 39 wherein said solvent is selected from isobutyl acetate, isopropyl acetate and ethyl acetate.

44. A process according to claim 39 wherein said solvent is selected from isobutyl acetate and isopropyl acetate.

45. A process according to claim 39 wherein said biomass extract is adsorbed onto silica gel prior to the step of contacting said biomass extract with said mixture.

* * * * *